(12) United States Patent
Martin (10) Patent No.: US 8,622,989 B2
(45) Date of Patent: Jan. 7, 2014

(54) DOSAGE CONTROL FOR DRUG DELIVERY SYSTEM

(75) Inventor: James F. Martin, Lebanon, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 173 days.

(21) Appl. No.: 13/038,841

(22) Filed: Mar. 2, 2011

(65) Prior Publication Data

US 2011/0152828 A1    Jun. 23, 2011

Related U.S. Application Data

(63) Continuation of application No. 11/695,775, filed on Apr. 3, 2007, which is a continuation of application No. 10/886,255, filed on Jul. 7, 2004, now abandoned.

(51) Int. Cl.
*A61M 31/00* (2006.01)

(52) U.S. Cl.
USPC .......................................................... 604/503

(58) Field of Classification Search
USPC ............... 604/65–67, 131, 503; 128/DIG. 12, 128/DIG. 13
See application file for complete search history.

(56) References Cited

U.S. PATENT DOCUMENTS

| | | |
|---|---|---|
| 5,069,668 A | 12/1991 | Boydman |
| 5,807,316 A | 9/1998 | Teeple, Jr. |
| 6,944,638 B1 | 9/2005 | Putnam |
| 7,727,194 B2 * | 6/2010 | Nalagatla et al. ............. 604/122 |
| 2003/0135087 A1 | 7/2003 | Hickle et al. |

FOREIGN PATENT DOCUMENTS

| | | |
|---|---|---|
| JP | 61-29364 A | 5/1994 |
| JP | 2001-509059 T | 7/2001 |
| JP | 2002-516692 T | 6/2002 |
| WO | WO 93/24893 A1 | 12/1993 |
| WO | WO 00/28217 A1 | 11/1999 |

OTHER PUBLICATIONS

PCT Search Report dated Feb. 21, 2006; International Application No. PCT/US2005/020149.
Norman Calvey, Norton E. Williams "Pharmacokinetics" *Principles and Practice of Pharmacology for Anaesthetists, Fifth Edition* Mar. 14, 2008, Wiley-Blackwell, XP002585747, pp. 23-42.
Kruger-Thiemer E: "Continuous Intravenous Infusion and Multicompartment Accumulation." *European Journal of Pharmacology* Oct. 1968 Lnkd-Pubmed: 5723425, vol. 4 No. 3, Oct. 1968, pp. 317-324, XP002585746 ISSN: 0014-2999.
Supplementary European Search Report dated Jun. 18, 2010 in corresponding application EP 05757429.

* cited by examiner

*Primary Examiner* — Manuel Mendez
(74) *Attorney, Agent, or Firm* — Verne E. Kreger, Jr.

(57) ABSTRACT

A method for delivering intravenous drugs to a patient comprising programming a drug delivery system, including a controller and an infusion pump, with a maintenance rate or a loading dose for a drug and causing the drug delivery system to (a) calculate a loading dose based on the maintenance rate or a maintenance rate based on the loading dose, (b) administer the loading dose of the drug to the patient to rapidly achieve a desired level of effect, and (c) administer the drug at a first maintenance rate to maintain the level of effect.

17 Claims, 9 Drawing Sheets

DOSAGE CONTROL FOR DRUG DELIVERY SYSTEM

CROSS REFERENCE TO RELATED PATENT APPLICATION

This is a continuation of U.S. patent application Ser. No. 11/695,775, filed on Apr. 3, 2007, which is a continuation of U.S. patent application Ser. No. 10/886,255, filed on Jul. 7, 2004, now abandoned.

FIELD OF THE INVENTION

The present invention relates generally to drug delivery systems, and more particularly to a method of calculating a drug infusion profile for a drug delivery system. While the invention can be used in administering a variety of intravenous drugs it is particularly useful as an anesthetic delivery system.

BACKGROUND OF THE INVENTION

Three conditions or objectives control the administration of an anesthetic, namely, to rapidly produce the desired pharmacologic effect (hypnosis, analgesia, etc.); to maintain the desired effect throughout the medical procedure; and to enable the patient to recover quickly from the effect following completion of the procedure.

In order to achieve the objective of rapidly inducing the desired anesthetic effect, the anesthesiologist typically delivers a so called "Loading Dose." A Loading Dose is a bolus (mg/kg, mg, etc.) of drug that rapidly brings the patient to a desired level of effect. In order to maintain the level of effect the anesthesiologist often uses an infusion pump to deliver a so called "Maintenance Rate." A Maintenance Rate is a constant infusion rate (µg/kg/min, mg/min, etc.) required to maintain the patient at a certain target, in this embodiment anesthetic, effect. The anesthesiologist may have to titrate this Maintenance Rate during the procedure as the patient's anesthetic needs change. A method that allows for rapidly adjusting the patient's level of effect is desired. Finally, in order to enable the patient to recover quickly from the anesthetic following completion of the procedure, the anesthesiologist attempts to deliver as little drug as needed. This can include tapering down the Maintenance Rate prior to the end of the procedure.

The term "anesthesia" is used herein to refer to the continuum of hypnosis and analgesia, achieved via anesthetic drugs, from anxiolysis through general anesthesia. In producing a level of anesthesia known as conscious sedation, as practiced by endoscopists, the anesthetic(s) is typically delivered through frequent boluses. This technique results in varying depths of anesthesia throughout the procedure. At times the patient may be so heavily anesthetized as to be classified in general anesthesia. At other times the patient may be under-anesthetized and exhibit pain and agitation. A patient responding to pain is uncooperative, making the procedure more difficult. As a result, the clinician tends to err on the over-anesthetized side. In addition to placing the patient at greater risk for adverse events, over-anesthetizing causes the patient's recovery from anesthesia to be much longer. Accordingly, a method is desired that enables the clinician to control the level of anesthesia without over- or under-anesthetizing the patient.

The term "sedation drug" is used herein to refer to the classes of drugs employed by anesthesiologists in inducing sedation including hypnotics and analgesics. Propofol and remifentanil are preferred drugs for sedation, principally due to their rapid onset and offset. However, this rapid action presents additional concerns for someone using an intermittent bolus technique, as typically done by non-anesthesiologists. With a rapid onset/offset more frequent boluses will be required. Consequently, anesthesiologists often use infusion pumps to continuously deliver these rapid action sedation drugs. However, non-anesthesiologists are not familiar with pharmacokinetic (PK) principals, and will have difficulty determining a Loading Dose/Maintenance Rate combination that will both rapidly achieve and maintain the desired level of anesthesia. The Anesthetic Delivery System (ADS) is intended to enable a non-anesthesiologist to safely and effectively use these rapid action anesthetic agents typically reserved for use by anesthesiologists.

What is desired is an algorithm that will allow the clinician to program an ADS with a desired maintenance rate, selected by the clinician to maintain a desired level of anesthesia, and then the ADS automatically calculates the appropriate sized loading dose based on the pharmacokinetics of the chosen sedation drug. The loading dose is then delivered by the ADS to rapidly achieve the level of sedation, immediately followed by a constant infusion of the sedation drug at the maintenance rate, to maintain the level of anesthesia. Moreover, a method is desired where the patient's level of anesthesia is rapidly adjusted, each time the clinician changes the maintenance rate, in response to the patient's changing anesthetic needs. Specifically, what is needed is an ADS that integrates the initiation and maintenance of anesthesia in an equation so that the appropriate sized loading dose may be calculated and administered to rapidly bring the patient's depth of anesthesia to a level maintained by the programmed maintenance rate. Further, when a change in the maintenance rate is requested, the dosage controller (DC) can calculate an incremental loading dose to rapidly achieve the new level of anesthesia.

SUMMARY OF THE INVENTION

In one embodiment, the invention provides a method of drug infusion for maintaining or rapidly adjusting a patient's level of anesthesia comprising programming an automated drug delivery system with a maintenance rate (MR); causing the drug delivery system to calculate the loading dose (LD) using a formula that relates loading dose and maintenance rate; the drug delivery system infusing the loading dose into patient to achieve a desired level of anesthesia and administering the drug at the maintenance rate to maintain the level of anesthesia.

In another embodiment, the invention provides a method of drug infusion for maintaining or rapidly adjusting a patient's level of anesthesia comprising the clinician programming an automated drug delivery system with a loading dose (LD); causing the drug delivery system to calculate the maintenance rate (MR) using a formula that relates loading dose and maintenance rate; the drug delivery system infusing the loading dose into the patient to achieve a level of anesthesia and administering the drug at the maintenance rate to maintain the level of anesthesia.

In a further embodiment, the level of anesthesia is rapidly adjusted when the clinician programs a new maintenance rate, by a method that further comprises: calculating the cumulative loading dose based on the drug already administered to the patient; calculating a new loading dose based on the cumulative loading dose and a new maintenance rate based on a formula relating loading dose and maintenance rate; the ADS infusing the new loading dose into patient to achieve the new level of anesthesia and the administering the drug at the desired new maintenance rate to maintain the new level of anesthesia.

Still a further embodiment is a drug delivery system that includes an infusion pump and a controller and is programmed to control infusion as described herein. In one embodiment, the system includes sensors for monitoring patient physiology and can be programmed to discontinue administering the drug if adverse physiology or trends are detected.

DETAILED DESCRIPTION OF THE INVENTION

For the purposes of illustration, the invention is explained using the delivery of propofol to achieve and maintain a level of anesthesia referred to as conscious sedation. However, the invention can be applied to any intravenous drug where it is appropriate to deliver a loading dose followed by a maintenance infusion. The equations will be adjusted for different pharmacokinetics (loading dose/maintenance rate relationships) for these other drugs. Examples of classes of drugs in addition to sedation drugs that can be administered in accordance with the invention are antibiotics, pain management drugs, cardiovascular drugs, anticancer drugs, and others.

A. Initiation of Sedation

An anesthetic drug such as propofol provides labeling recommendations for initiating sedation (loading dose)–0.0 to 0.5 mg/kg, and infusion rates for maintaining the patient's level of sedation (maintenance rate)–0.0 to 75 µg/kg/min. DC is designed to correlate these two ranges, such that a clinician simply enters a maintenance rate (MR) and DC will calculate the appropriate loading dose (LD) with the following equation in the case of propofol:

$$LD=0.5*W*(MR/75)$$

where,
LD=loading lose (mg),
MR=maintenance rate (µg/kg/min),
W=weight (kg) of the patient
0.5=0.5 mg/kg
75=75 µg/kg/min.

For other drugs, and application, similar correlations can be developed. While these correlations will often be defined in terms of the weight of the patient, this does not have to be true for all cases. Some drugs may have dosages that are less dependent or essentially independent of patient weight for typical patients. The equation that has been developed for propofol above is based on the maximum loading dose (0.5 mg/kg) recommended for the drug and the therapy (e.g., conscious sedation) in which the drug is used and the maximum maintenance rate (75 µg/kg/min). In this case the formula is a linear proportion or linear interpolation. The clinician may select a maintenance rate corresponding to the level of anesthesia he desires to achieve, e.g., ASA guidelines are drafted in terms of mild, moderate and deep anesthesia and based on the ratio of that maintenance rate to the maximum maintenance rate recommended for that application of the drug, a loading dose is determined. Thus, in accordance with certain embodiments of the invention, the equation relating loading dose to maintenance rate will represent a linear proportion or interpolation based on the loading dose and maintenance rate ranges suggested by the supplier and still more specifically based on the maximum loading dose and maintenance rate suggested by the supplier. These ranges may be therapy specific, for example, a different proportion or interpolation based on the drug label's recommended loading dose and maintenance rate for that therapy would be used if general anesthesia as opposed to conscious sedation was the objective. The loading dose calculation flow chart is provided in FIG. 2F where the calculation based on the maximum label dose is shown as program step 260.

Figure 1:
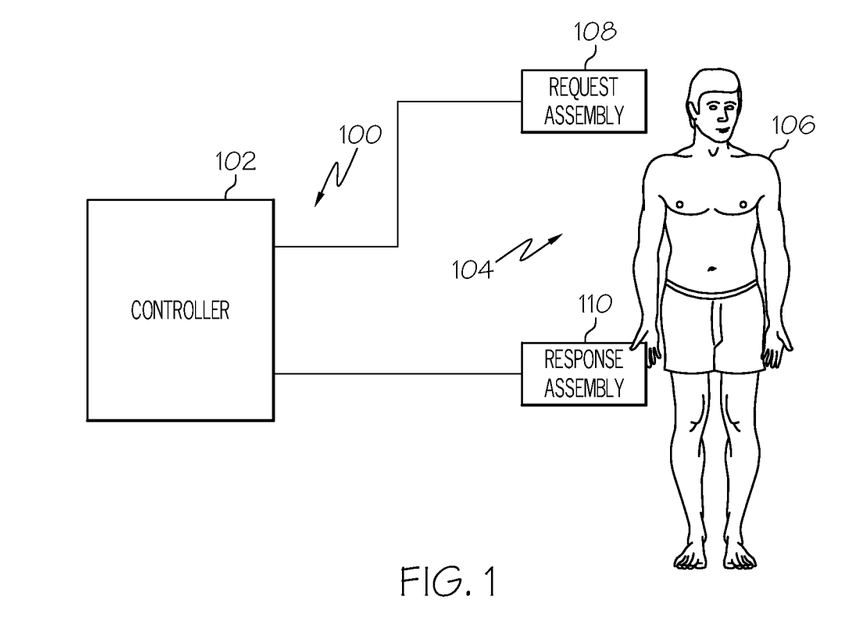
FIG. 1 is a drawing of the Automated Response System (ARM) utilized in an embodiment of the invention.
Figure 2A:
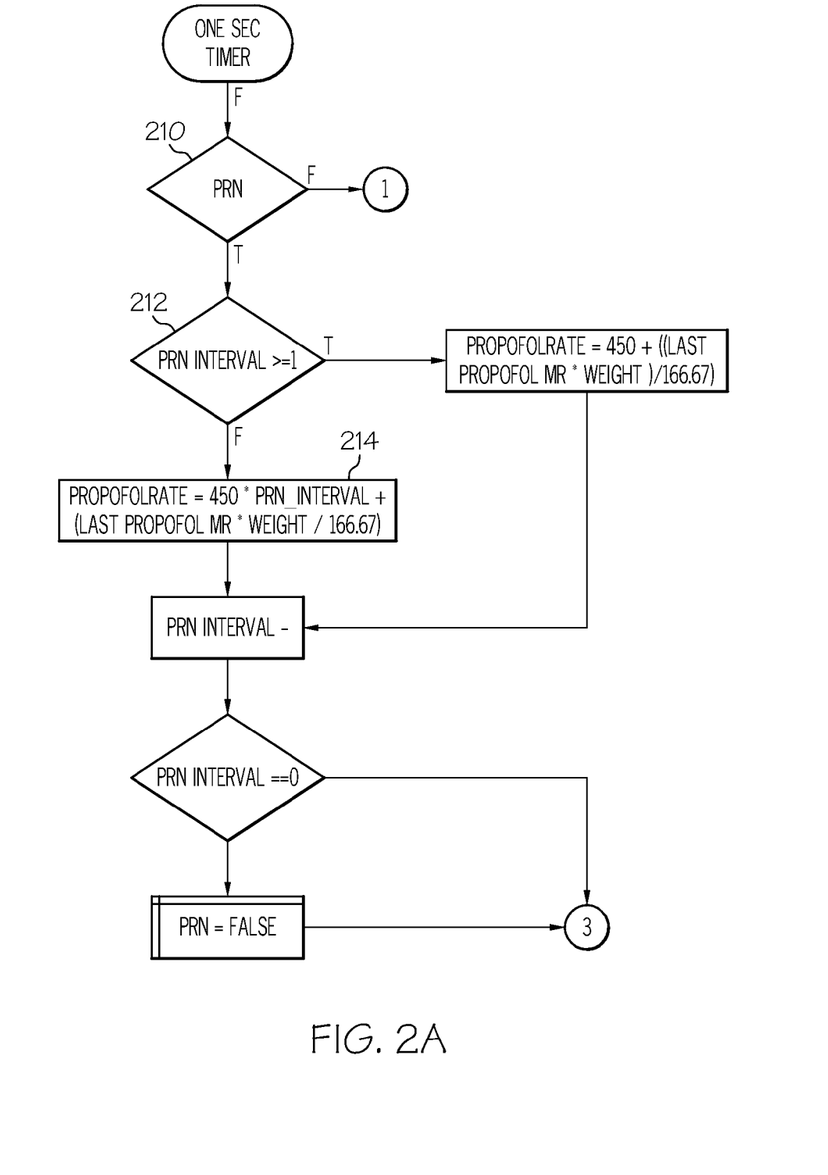
FIG. 2 is a collection of flow charts (FIGS. 2A-2F) for a DC program useful in accordance with an embodiment of the invention.
Figure 2B:
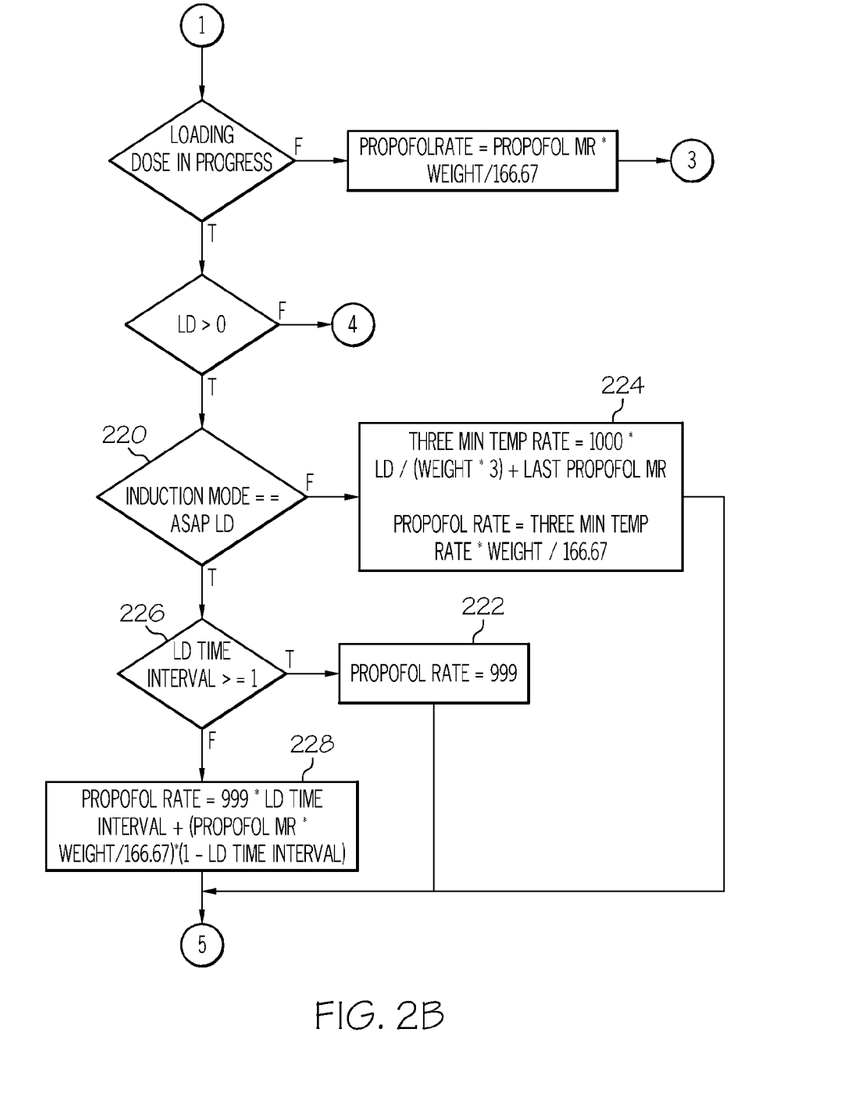

After the loading dose (LD) has been calculated, the anesthetic delivery system (ADS) will automatically deliver it, prior to starting the maintenance rate (MR). As shown in FIG. 2B, the loading dose can be administered in a rapid induction model or a controlled induction model (see program determination 262).

1. Rapid Induction

In one embodiment illustrated in program step 222 in FIG. 2B, the ADS can deliver the LD at the maximum pump rate. For the purpose of illustration, 999 ml/hr will be used as the maximum pump rate. DC first calculates the time required (seconds) to deliver the LD at 999 ml/hr:

$$LD\_time=3600*LD/(10*999)$$

where 3600 is the conversion from hours to seconds (sec/hr) and 10 is the concentration of the propofol solution (mg/ml). The LD_time is then converted into sampling intervals. For the purpose of illustration only, a sampling interval of 1.5 seconds will be used:

$$LD\_intervals=LD\_Time/1.5$$

If the number of LD_intervals is not an integer, then DC calculates the infusion rate (ml/hr) for the last interval (program step 228) to deliver the remainder of the LD using the equation:

$$IR\_LD\_remain=999*Interval\_remain+MR\_ml/hr*(1-Interval\_remain)$$

where, $$MR\_ml/hr=MR*W/166.67=\text{Maintenance Rate in ml/hr}$$

$$Interval\_remain=LD\_intervals-INTEGER(LD\_intervals)$$

Note that the 166.67 is the conversion based on 60 min/hr, and 1,000 µg/mg, and 10 mg/ml (propofol concentration).

The ADS then delivers the loading dose for INTEGER (LD_Intervals) at a pump rate 999 ml/hr, and then delivers at IR_LD_remain for one interval. This is shown if FIG. 2B in program steps 226 and 228. Immediately following the completion of the LD, the ADS starts delivery of the MR (actually at a pump rate of MR_ml/hr).

2. Controlled Induction

In an alternative embodiment illustrated in FIG. 2B at program step 224, the ADS can deliver the LD over a specified period of time, with a decreasing ramp that culminates at the maintenance rate. For the purpose of illustration, 3 minutes (180 seconds) will be used as the Controlled Induction time.

First, DC calculates the infusion rate (µg/kg/min) required if the LD were delivered at a constant rate over those 3 minutes:

$$Temp\_rate=1000*LD/(W*3)$$

where, 1000 is conversion from mg to ng.

Figure 3:
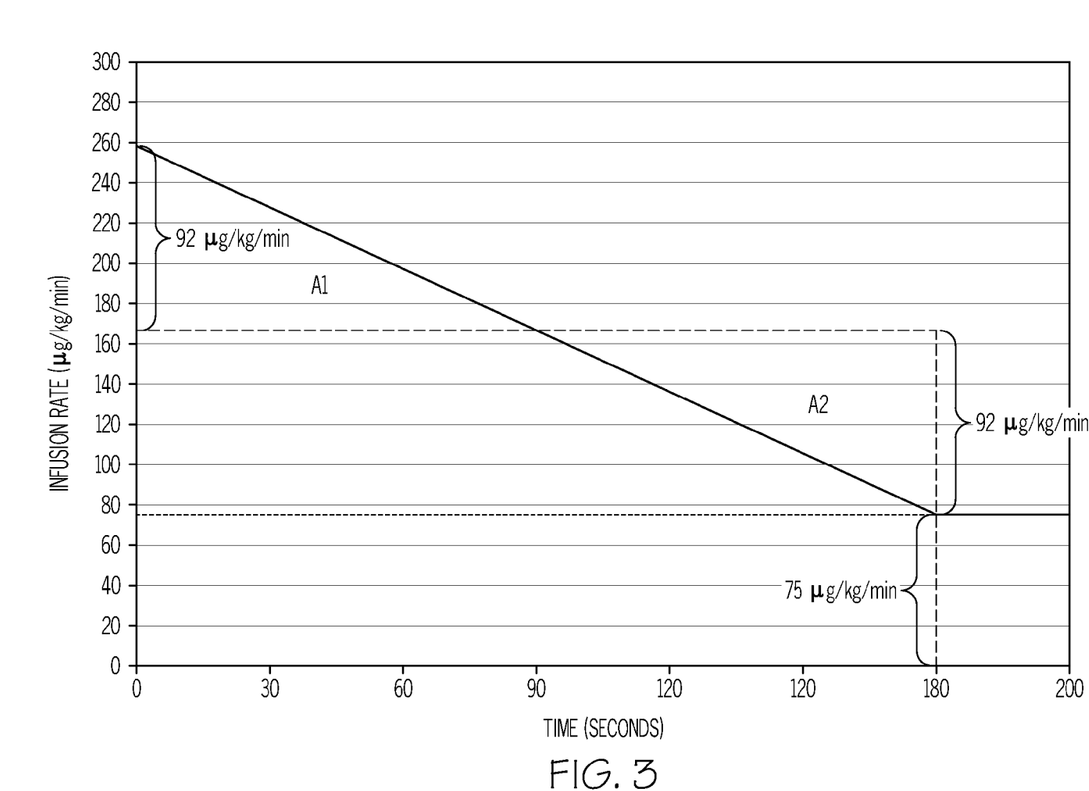
FIGS. 3 and 4 are graphs illustrating the determination of a ramped infusion rate for a loading dose that culminates in the maintenance rate.

As shown in FIG. 3, the area of the rectangle (dashed line in FIG. 3) defined by the Controlled Induction period (180 seconds) and the Temp_rate equals the LD. For this embodiment, the objective is to calculate a ramp, such that the area under the ramp is equal to the area of the rectangle defined by the Temp_rate. This is accomplished with basic geometry. First, since the ramp terminates into the Maintenance Rate (dotted line at 75 µg/kg/min in FIG. 3) at the end of the Controlled Induction period, the area under the Maintenance Rate can be ignored for the following analysis—so the focus can be on the areas above the MR. Then, if the ramp is such that the height of the ramp is equal to two times the height of the rectangle (above the MR) then the area under the ramp is equal to the area under the rectangle. This is illustrated in FIG. 3: A1=A2, therefore the area of the triangle equals the area of the rectangle.

Figure 4:
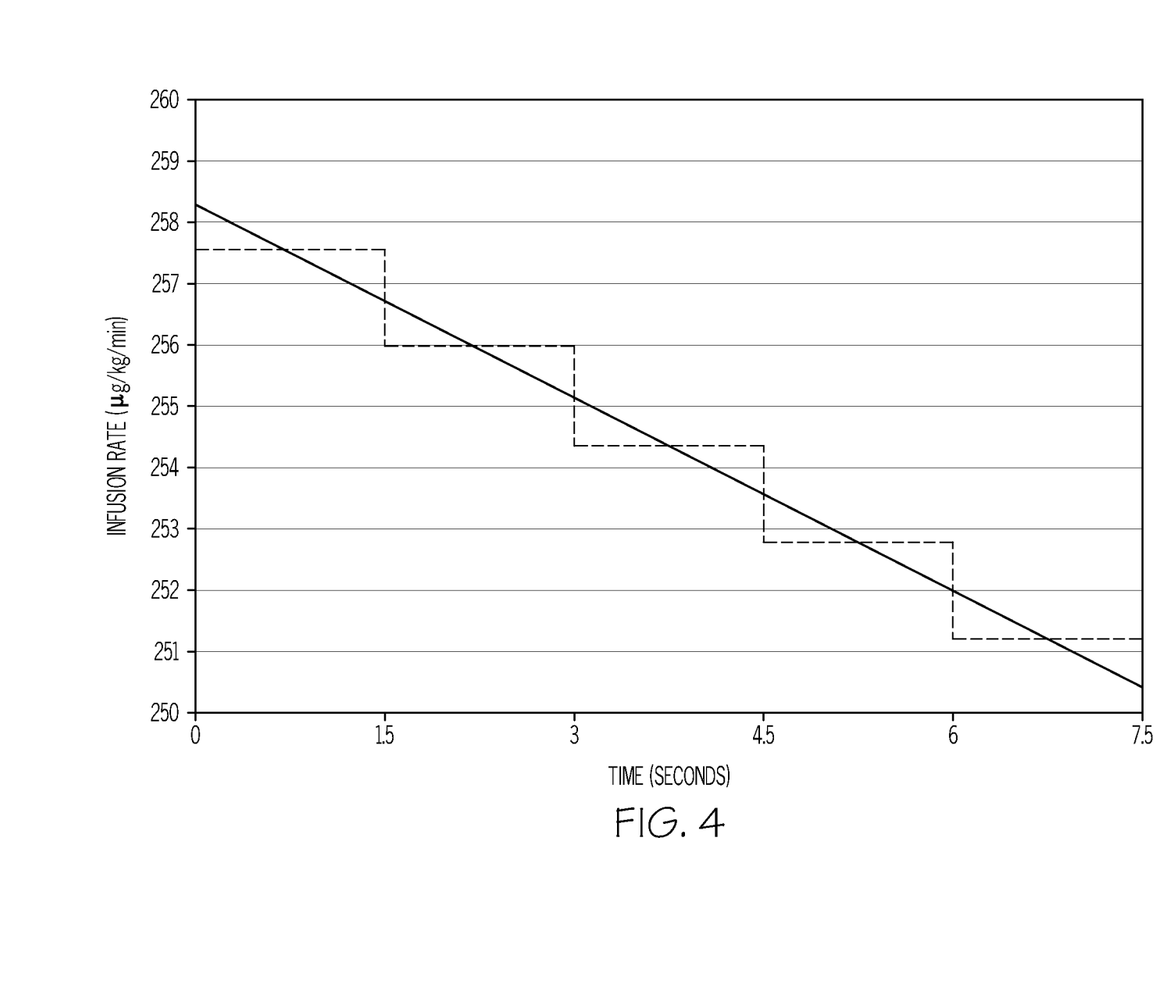

The DC first calculates the difference (Delta) between the Temp_Rate and the MR:

$$Delta=Temp\_rate-MR$$

then in this example, the starting rate (µg/kg/min) for the ramp would be $$2*Delta$$

and the slope (µg/kg/min/min) of the ramp in this example would be $$Slope=2*Delta/3$$

where 3 is the induction period. However, this assumes a continuous ramp. The DC ramp is actually a series of decreasing steps (each step defined by the sampling interval, which is 1.5 seconds in this illustration). The area under this "staircase" must equal the area under the ramp, in order for the LD to be correct. The same geometrical principal applied above applies here as well, and is illustrated in FIG. 4. If the height of each step is equal to the average height of the ramp over the step interval the areas will be the same.

Therefore, the starting rate (µg/kg/min) for the ramp is more correctly expressed as:

$$Start\_IR=MR+2*Delta-(Slope/2)/40$$

where 40 is the number of samples taken over a minute (1.5 second intervals)—converting the slope from "per minute" to "per interval."

The ADS delivers the LD starting at Start_IR and then ramps down the infusion rate, each sample, over the next 3 minutes:

$$LD\_IR=Start\_IR-Slope*Interval\_count/40$$

$$Interval\_count_x=Interval\_count_{x-1}+1$$

where, Interval_count is a counter tracking the progression of the 120 samples in the 3 minute period. At the end of the 3 minutes the infusion rate will be equal to the MR selected by the user, and the ADS will continue to deliver the MR.

It is important to note that all the calculations are in µg/kg/min, therefore before sending the rate to the pump it must be converted into ml/hr. The standard equation for converting from µg/kg/min to ml/hr is:

$$IR\_ml/hr=IR*W/166.67$$

In another embodiment for the Controlled Induction, DC could simply deliver the Temp_Rate over the entire time period, then switch to the Maintenance Rate. This embodiment is illustrated in FIG. 2B of the flow chart. In the illustrated embodiment, the system gives the clinician the option in program step 220 of selecting between the rapid induction mode 222 or the controlled induction mode 224.

The method described above basically portrays how anesthesiologists, who are trained in pharmacokinetic principals, sedate a patient. The DC is advantageous because it automatically correlates the loading dose with the maintenance rate (or vice versa) so that only one variable is needed to compute the other. For example, whereas in the prior art, the physician needed a value for both the loading dose and the maintenance rate in order to rapidly initiate and maintain sedation, a ADS using the DC is able to calculate the appropriate loading dose based on a given maintenance rate. Thus, by entering the desired maintenance rate for the patient, DC automatically calculates the loading dose needed to rapidly bring the patient's level of sedation to the selected maintenance rate. The loading dose is administered followed by the constant infusion at the specified maintenance rate.

Conversely, the DC can also calculate a maintenance rate based on a given loading dose value.

$$MR=75*LD/(0.5*W)$$

B. Adjusting Level of Sedation

DC also allows for rapid adjustment to a new level of sedation when the clinician programs a new maintenance rate. In prior methods of drug infusion, if an anesthesiologist intra-procedurally decides to change the patient's level of sedation, he will typically adjust only the infusion rate, and not deliver another loading dose. This results in a slower adjustment from the present level of sedation to the new level of sedation. However, DC can calculate an incremental loading dose for each change in maintenance rate. This results in a significantly quicker adjustment because delivering an additional bolus rapidly brings the patient to the new level of sedation.

1. Incremental and Cumulative Loading Dose

Figure 2C:
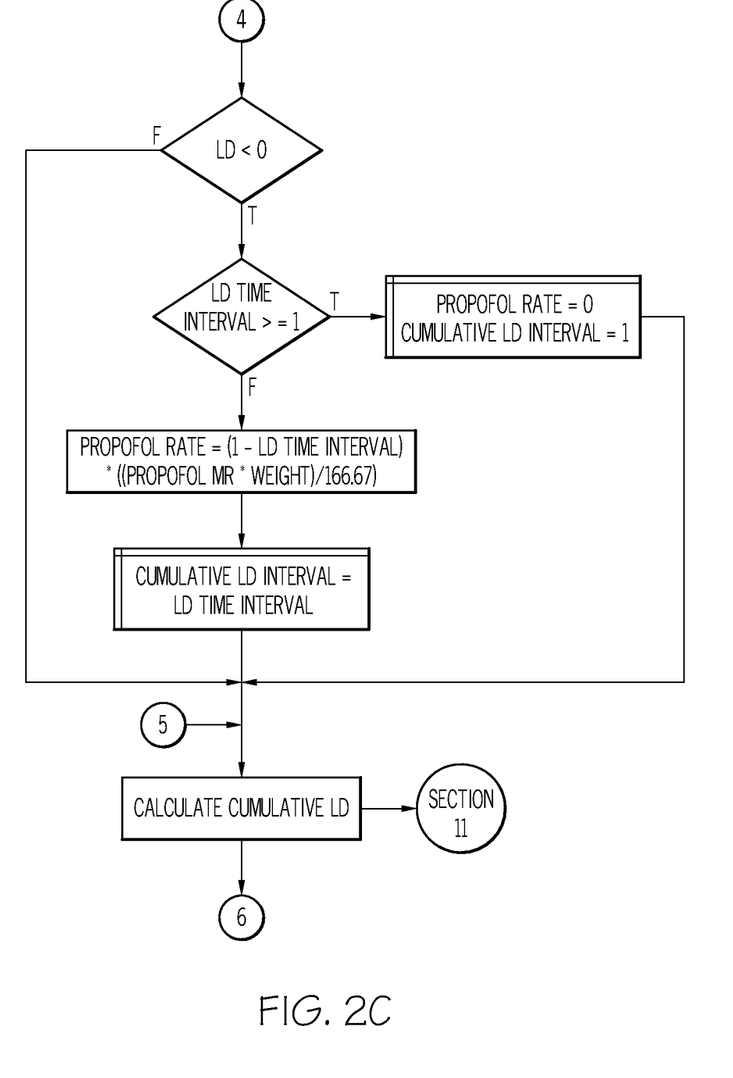
Figure 2D:
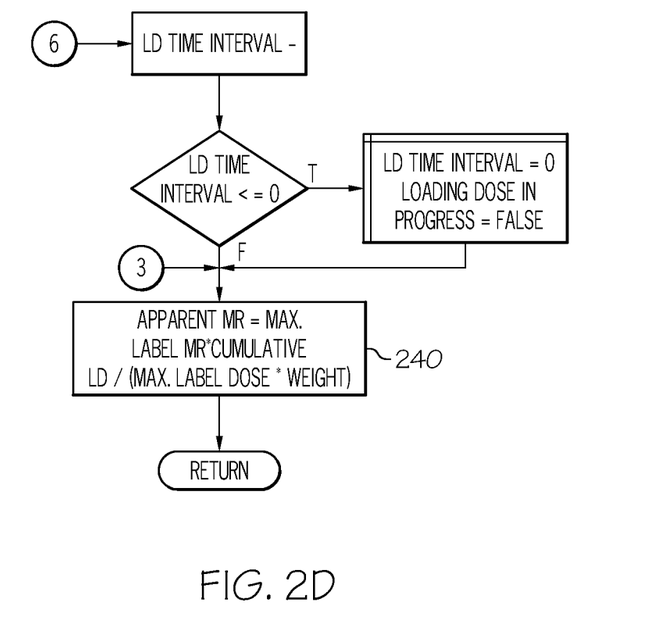

In accordance with the invention, a correlation is established between loading dose and maintenance rate. Based upon this correlation, by tracking the accumulated loading dose, the ADS can quickly define a bolus or incremental loading dose that will rapidly produce a level of sedation that is consistent with the new maintenance rate. The clinician programs changes in the level of sedation he or she desires by inputting a new maintenance rate that the clinician associates with the desired level of sedation. Each time a maintenance rate change is requested, DC will calculate the loading dose required for the new maintenance rate based on the equation above and then subtract the total loading doses previously given (cumulative loading dose–LD_cum) as shown in FIG. 2F step 262 to compute the incremental loading dose value to be administered to the patient.

$$Incremental\ LD=0.5*W*(MR\_new/75)-LD\_cum$$

Before starting the new maintenance rate, the ADS will deliver this "incremental" loading dose to rapidly bring the patient from the present level of sedation to the new level, and then maintain this new level of sedation at the new maintenance rate.

Figure 2E:
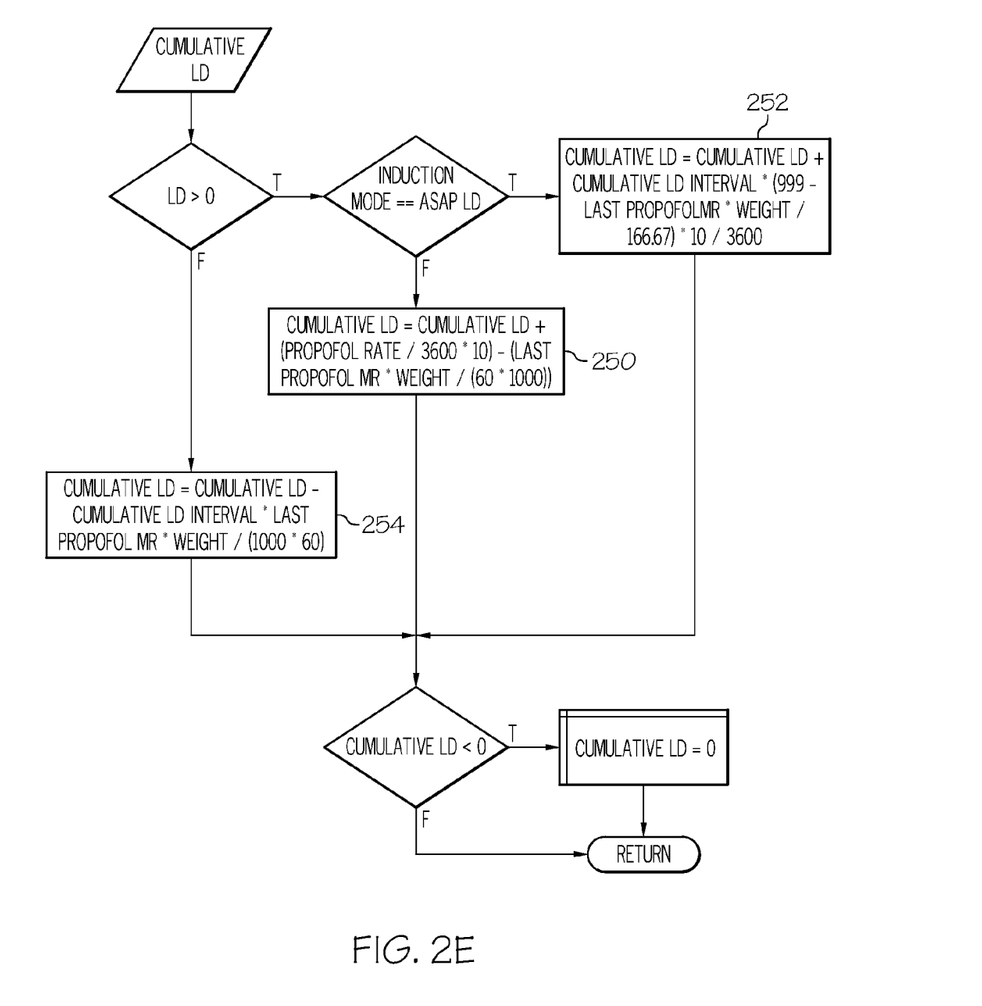
Figure 2F:
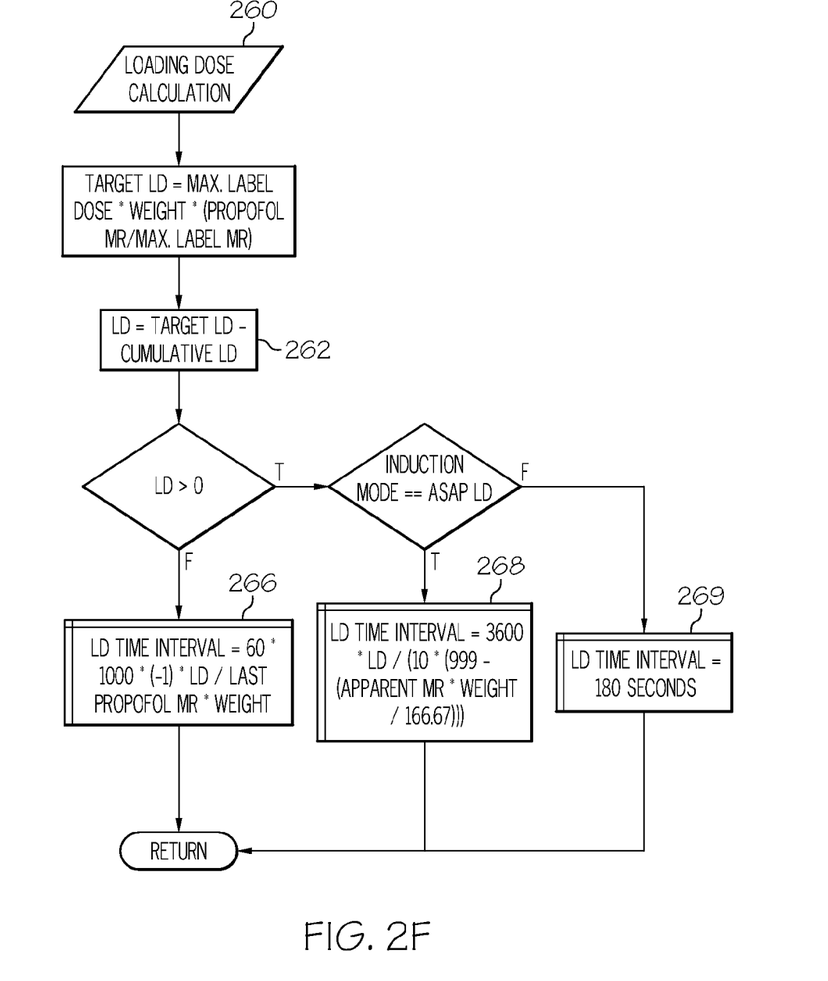

The Cumulative Loading Dose may be computed as shown in FIG. 2E by the following formula:

$$LD\_cum_x=LD\_cum_{x-1}+\text{amount of } LD \text{ delivered during sample}$$

Thus, the loading dose needed to rapidly increase the patient from the present level of sedation to the new level of sedation, i.e. the incremental loading dose, is calculated by calculating an initiation loading dose for the new maintenance rate and then subtracting the cumulative loading dose already delivered to the patient as shown in FIG. 2F, step 262. FIG. 2E illustrates the calculation of the cumulative loading dose. In the illustration the cumulative loading dose is adjusted to add the amount of loading dose added during a sample interval. Calculation of the cumulative loading dose when the addition of the incremental loading dose is made by the rapid induction method is shown at program step 252 in FIG. 2E. Alternatively, this addition can occur using the controlled induction as shown in program step 250 in FIG. 2E. When the loading dose is negative, the cumulative loading dose is reduced as shown at 254.

For the purpose of illustration, assume that to achieve a level of sedation corresponding to maintenance rate of 50 μg/kg/min requires an initiation loading dose of 0.33 mg/kg, and to achieve a level of sedation corresponding to maintenance rate of 75 μg/kg/min requires an initiation loading dose of 0.50 mg/kg. When the drug is being administered at a current maintenance rate of 50 μg/kg/min and the physician desires to increase the patient's level of sedation with a maintenance rate of 75 μg/kg/min, DC would calculate an incremental loading dose of 0.50-0.33=0.17 to bring the patient to a level of sedation corresponding to the new maintenance rate of 75 μg/kg/min. Essentially, the incremental loading dose required to bring the patient to the level of sedation corresponding to new maintenance rate is calculated by taking the difference between the initiation loading dose required to bring a patient to a specified maintenance rate (e.g. LD=0.50 mg/kg for MR=75 μg/kg/min) and the cumulative loading dose already administered to the patient (present MR=50 μg/kg/min, LD was 0.33 mg/kg). Thus, to bring the patient from MR=50 to MR=75, the cumulative LD administered to the patient for MR=50 (0.33 mg/kg) is subtracted from the initiation LD for MR=75 (0.50 mg/kg) to get the incremental loading dose of 0.17 mg/kg. Accordingly, an incremental loading dose of 0.17 should be given to increase the patient from the present level of sedation to the new level of sedation. The new $LD_{cum}$ would then be 0.50 mg/kg which would be used to calculate a new incremental loading dose if another new maintenance rate is desired.

The "administration" of the incremental loading dose during a procedure when a physician decides to increase the maintenance rate, differs from when a physician decides to decrease the present maintenance rate as further described below.

2. Increase in Maintenance Rate: Rapid Induction

During the procedure, the physician may determine that the patient is under-sedated and increase the maintenance rate. In order to rapidly bring the patient's level of sedation to the new level of sedation, an incremental loading dose will be delivered to the patient.

In the Rapid Induction embodiment, the ADS will deliver the LD as quickly as possible, setting the pump rate to a maximum rate (e.g., 999 ml/hr) until the LD is delivered. However, unlike the initiation LD, in this case DC must deliver the LD on top of an existing MR and the existing infusion rate must be accounted for in the calculation of the LD time.

The formula to determine the length of time to deliver the LD at 999 ml/hr is:

$$LD\_time = 3600*LD/(10*(999-MR\_ml/hr))$$

where MR_ml/hr=MR*W/166.67, and MR is not the new maintenance rate, but it is the existing maintenance rate, prior to the change. At the end of the LD, once the ADS starts delivering the new maintenance rate (MR_new), the variable will be reset. This is illustrated in FIG. 2F, at step 268.

LD_time is converted into intervals (again using 1.5 seconds for this illustration):

$$LD\_intervals = LD\_time/1.5$$

Again, if LD_intervals is not an integer, DC must calculate the infusion rate required to deliver the remainder of the LD during the next sample interval:

$$IR\_LD\_remain = 999*Interval\_remain + MR\_new\_ml/hr*(1-Interval\_remain)$$

where, $$Interval\_remain = LD\_intervals - INTEGER(LD\_intervals)$$

and MR_new_ml/hr is the new maintenance rate converted to ml/hr.

The ADS will deliver the loading dose at a pump rate of 999 ml/hr for INTEGER(LD_intervals) and then at an infusion rate of IR_LD_remain for one sample. After delivering the LD the ADS will set MR to MR_new, and begin delivery of the new maintenance rate.

These equations are basically identical to the equations for the initial Loading Dose delivery. If at start up both LD_cum and MR are set to zero, and the initial maintenance rate is treated as MR_new, then the same equation can be used for all Rapid Induction maintenance rate increases.

3. Increase in Maintenance Rate: Controlled Induction

In the Controlled Induction embodiment the ADS will deliver the LD over the specified time period (3 minutes for illustration) on top of the existing MR. See step 269 in FIG. 2F. As with an initiation LD, DC calculates infusion rate (μg/kg/min) required as if the LD is to be delivered at a constant rate:

$$Temp\_rate = 1000*LD/(W*3) + MR$$

Again the maintenance rate value is not the new maintenance rate (MR_new), but the rate prior to changing the maintenance rate. In this way, the loading dose is being administered on top of the existing maintenance rate.

DC then calculates the difference between this Temp_Rate and the MR_new:

$$Delta = Temp\_rate - MR\_new$$

The starting rate (μg/kg/min) for the ramp is then:

$$Start\_IR = MR\_new + 2*Delta - (Slope/2)40$$

and the slope of the ramp (μg/kg/min/min) is:

$$Slope = 2*Delta/3$$

The ADS delivers the LD starting at Start_IR and then ramps down the infusion rate, each sample, over the next 3 minutes:

$$LD\_IR = Start\_IR - Slope*Interval\_count/40$$

$$Interval\_count_x = Interval\_count_{x-1} + 1$$

where, Interval_count is a counter tracking the progression of the 120 samples in the 3 minute period. At the end of the 3 minutes the infusion rate will be equal to the MR_new, and DC will set MR=MR_new and continue to deliver the new maintenance rate.

These equations are similar to the equations for the initial Loading Dose delivery. If at start up both LD_cum and MR are set to equal zero, and the initial Maintenance Rate is set as MR_new then the same equation can be used for all Three Minute Induction Maintenance Rate increases.

In an alternative embodiment the incremental LD can delivered at a constant rate over the "controlled induction" period.

4. Decrease in Maintenance Rate

If the maintenance rate is decreased (e.g., if the clinician feels the patient is over-sedated) the incremental loading dose will be negative. However, it is not possible to withdraw drugs from the patient. Calculation of a negative loading dose is shown in FIG. 2C. To simulate a negative loading dose, the DC calculates the period of time it would take to deliver that negative dose at the existing maintenance rate based on the formula:

$$Zero\_time=60*1000*LD/(MR*W)$$

where, 1000 is a conversion from mg to µg, 60 is conversion from minutes to seconds, and MR is the existing maintenance rate prior to the change, not the new maintenance rate (MR_new). This is shown in FIG. 2F at program step 266. The cumulative loading dose is also decreased as shown in program step 254 in FIG. 2E.

This time is converted into sampling intervals. For the purpose of illustration a sampling interval of 1.5 seconds will be used:

$$Zero\_intervals=Zero\_time/1.5$$

Again, if Zero_intervals is not an integer, DC calculates the infusion rate required to deliver the remainder of the LD during the last sample:

$$IR\_zero\_remain=MR\_new\_ml/hr*(1-Interval\_remain)$$

where, $$Interval\_remain=Zero\_intervals-INT(Zero\_intervals)$$

The ADS will stop delivery of propofol for INT(Zero_intervals) and then begin infusing at an infusion rate of IR_zero_remain for one sample. After completing the LD, the ADS will set the maintenance rate to MR_new, and begin delivery of the new maintenance rate.

C. Intra-Procedure Bolus of Propofol

During the procedure the physician may decide that a transient increase in sedation is required. In this case, a physician typically administers a bolus that temporarily increases the patient's level of sedation. For example, if during a surgical procedure, a more sensitive part of the procedure is about to be performed, the physician may give a bolus to raise the patient's level of sedation temporarily. In this case, the maintenance rate remains the same. When the transient increase in sedation is over, the level of sedation returns to the level defined by the previous maintenance rate. Because the maintenance rate remains the same, an intra-procedure bolus does not affect the cumulative loading dose calculation. FIG. 2A shows in program step 210 the determination that the bolus (PRN) is an intra-procedure addition that does not affect the loading dose.

When the physician asks for a bolus, DC will calculate a fixed bolus (mg), for example:

$$Bolus=0.25*W$$

In this example of DC, 0.25 was used as an illustration, however, any number from 0 to 0.5, which represents the loading dose range recommended by the pharmaceutical supplier, could have been chosen (exceeding 0.5 would mean that a single bolus would be larger than the maximum recommended LD for initiating sedation with propofol). Since the bolus will be delivered in addition to the existing maintenance rate the equations for delivering a Rapid Induction loading dose during an increase in maintenance rate can be used here.

$$Bolus\_time=3600*Bolus/(10*(999-MR\_ml/hr))$$

This time is converted into intervals at program step 212:

$$Bolus\_intervals=Bolus\_time/1.5$$

Again, if Bolus_intervals is not an integer, in program step 214 DC can calculate the infusion rate required to deliver the remainder of the Bolus during the next sample:

$$IR\_B\_remain=999*Interval\_remain+MR\_ml/hr*(1-Interval\_remain)$$

where, $$Interval\_remain=Bolus\_intervals-INTEGER(Bolus\_intervals)$$

The ADS will deliver the Bolus at a pump rate of 999 ml/hr for INTEGER (Bolus_intervals), and then at an infusion rate of IR_B_remain for one sample. After delivering the Bolus, the DC will renew the delivery of the maintenance rate.

In an alternative embodiment the bolus can be delivered over a fixed time interval, similar to a Controlled Induction delivery of a LD during a maintenance rate increase.

D. Examples

Non-limiting examples of various implementations of the above-described embodiments of the invention are provided below:

1. If the physician changes the maintenance rate immediately after a maintenance rate change (i.e. during the delivery of a Rapid Induction LD), in one embodiment, DC calculates an "apparent maintenance rate" based on the Cumulative loading dose delivered at that time:

$$MR\_apparent=75*LD\_cum/(0.5*W)$$

This calculation is used in program step 240 in FIG. 2D.

The cumulative loading dose here would be equivalent to the cumulative loading dose at the old maintenance rate plus the total amount of loading dose delivered during the Rapid Induction prior to when the physician changed the maintenance rate during the Rapid Induction as shown in FIG. 2E program step 252.

In accordance with one embodiment, DC next treats this change as a standard rate change (either increase or decrease) from the apparent maintenance rate to the new maintenance rate. The standard formulas as discussed above are used.

2. If the physician changes the maintenance rate during a Controlled Induction (for example, 3 minutes for illustration purposes), the loading dose will still be delivered in the original 3 minute period. In the embodiment where the LD is delivered at a constant rate over the Controlled Induction period, a new constant infusion rate is calculated, that will deliver the new incremental LD over the remaining time.

In the embodiment where the Loading Dose is delivered via a decreasing ramp, the Dosage Controller must recalculate a slope and initial infusion rate. To accomplish this, DC uses a counter that is triggered in the Controlled Induction mode. It is called Ramp_counter and is initialized at 120 (180 minutes in 1.5 second intervals). Then the equations for the Temp_rate and Slope in the Controlled Induction mode become:

$$\text{Temp\_rate} = 1000*LD/(W*(3*\text{Ramp\_counter}/120)) + MR$$

$$\text{Slope} = 2*\text{Delta}/(3*\text{Ramp\_counter}/120).$$

The rest of the equations may remain unchanged.

Every interval during the Controlled Induction Ramp_counter is decreased by 1, reaching 0 at the end of the 3 minutes, and Interval_count is increased by 1. If the physician changes the maintenance rate during the Controlled Induction, the equation to calculate the new constant rate and slope uses the current value of the Ramp_counter—it is not reset to 120. In this manner there is an immediate change to a new Start_IR, ramping down to the MR_new at a new slope. This holds for both rate increases and decreases (depending on how much of the original loading dose was delivered, there may still be some LD to deliver despite a decrease in the MR). If the calculated LD is negative, the DC switched to the Time_zero mode.

In a further embodiment, the DC can be configured to require any change during a Controlled Induction to start a new 3 minute clock. In this case the original 3 Minute Induction equations would be used.

3. If a bolus is selected during delivery of a loading dose, the loading dose can be interrupted as the ADS delivers the bolus. Immediately after delivering the bolus the loading dose is resumed where it left off.

4. If the maintenance rate is changed during the delivery of a bolus, the DC notes the maintenance rate change request, but continues with the delivery of the bolus. Immediately after the bolus has been delivered, the DC switches into a new maintenance rate mode.

E. Supervisory Features

The concepts of the cumulative loading dose and the apparent maintenance rate also enable DC to be effectively integrated into a comprehensive Supervisory Shell. A Supervisory Shell is a function embedded in automated drug delivery systems that is designed to monitor drug delivery based upon control parameters in addition to the maintenance rate and loading dose correlation discussed above. Elements of a Supervisory Shell can include (but are not limited to):

Infusion rate limits

Stopping drug delivery if adverse physiology or trends occur

Reducing drug delivery if certain conditions are met

Potentially increasing drug delivery under certain circumstances

Modifying controller parameters based on certain events (this applies more to closed loop systems).

1. If a Supervisory Shell is designed to turn off drug infusion in response to adverse physiology, the DC can treat this as a normal decrease in maintenance rate (stopping infusion is considered as a "decrease to zero"). A Zero_time will be calculated, and the cumulative loading dose will be integrated down every interval. At the end of the Zero_time the cumulative LD will equal zero. When the adverse event clears (physiology returns to normal) the clinician will likely re-establish drug infusion at a new maintenance rate. If this occurs prior to the end of the Zero_time, the DC may treat it as a change in MR from the apparent MR (at the time the clinician decided to re-start infusion) to the new MR. If the new MR is greater than the apparent MR it will be treated as a MR increase. If the new MR is less than the apparent MR it will be treated as a decrease (negative LD).

The clinician can choose either a Rapid or a Controlled Induction, however, if the LD is negative DC defaults to the Time_zero format. In addition, the clinician does not necessarily have to wait until the adverse physiology clears before re-starting drug delivery.

2. If the adverse event occurred during the delivery of a loading dose and the Supervisory Shell stopped drug delivery DC would use the apparent MR at the time the infusion was stopped, to calculate the Zero_time.

3. A Supervisory Shell may be designed to reduce drug delivery in response to certain conditions—such as adverse trends. If the Supervisory Shell simply requests a fixed reduction (say 20% for example) in the maintenance rate DC will handle this as a standard MR decrease. An alternative way to integrate DC within a Supervisory Shell to reduce infusion rate in response to an adverse trend, is to take advantage of the apparent maintenance rate concept and tune the size of the infusion rate reduction to the severity of the patient's condition, as indicated by the trend. Specifically, upon detecting worsening physiology the Supervisory Shell can instruct DC to set the MR to zero. This will cause DC to calculate a Time_zero and begin integrating down the cumulative LD. When the condition clears (physiology returns to normal) the Supervisory Shell can inform DC to re-establish drug delivery at the apparent MR (which exists at the time the physiology returns to normal). In this manner, the longer the patient's physiology is trending poorly, the larger the reduction in the infusion rate.

4. A Supervisory Shell may also be designed to temporarily stop drug delivery if it detects a correctable problem within the ADS. These problems could include (but not limited to) a dislodged pulse oximeter probe, a disconnected ECG lead, air-in-line detected in the infusion line, or IV bag/vial empty. If the Supervisory Shell stops delivery of drug in response to such a problem, DC first saves the present maintenance rate then performs a decrease in maintenance rate, with the new MR being zero. When the clinician corrects the problem, DC calculates the apparent maintenance rate based on the cumulative loading dose at the time the problem is corrected. Then DC performs an increase in maintenance rate (in the Rapid Induction mode preferably) from the apparent maintenance rate to the saved maintenance rate.

Without the concepts of the cumulative loading dose and the apparent maintenance rate, a drug delivery system would have to rely on simple changes to the maintenance rate. There would not be any loading doses (negative or positive) enabling the rapid achievement of the new level of sedation. Therefore, there could be extended periods of time when the patient is inadequately cared for.

F. Integration of DC and an Automated Responsiveness Monitor

Due to patient-to-patient variability IV drugs are typically titrated to clinical effect—the clinician must tune the infusion rate to achieve the target effect on each individual patient. Further, as the patient's needs change during the course of a medical procedure, the clinician will have to titrate the drug to maintain a desired target effect. For well-characterized physiologic parameters, such as blood pressure, there are continuous monitors that a fully automated drug delivery system can use to close-the-loop and automatically perform this titration for the clinician. For most physiologic parameters the "loop" cannot be closed—this includes sedation/anesthesia.

In one embodiment the ADS may include a means of assessing a patient's level of sedation—the Automated Responsiveness Monitor (ARM). Integrated with the ARM and a Supervisory Shell, the DC will enable the clinician to more easily titrate the delivery of propofol to each individual patient. One method of using ARM comprises applying a vibration stimuli or request for a predetermined response to the patient; instructing the patient to respond to the vibration stimuli; and monitoring the patient's response to the vibration stimuli. This action is repeated at a predetermined interval throughout the medical procedure The use of ARM to assess a patient's level of sedation is described in detail in commonly assigned U.S. patent application Ser. No. 10/674,160 filed Sep. 29, 2003 which is herein incorporated by reference. As described in the applications, there are many methods and apparatuses associated with ARM. In sum, ARM is a patient response system that sends various requests to a patient to receive a patient's response and then analyzes the patient's responses to the requests. By analyzing the patient's responses, the patient's level of sedation can be determined. An example of how ARM works is shown in the drawings. FIG. 2 illustrates a conscious sedation system 100 including a controller 102 and a response testing apparatus 104. The controller 102 generates a request for a predetermined response from a patient 106 and analyses at least a response generated by the patient 106 to the request to determine a level of sedation of the patient 106. The response testing apparatus 104 includes a request assembly 108 and a response assembly 110. The request assembly 108 communicates to the patient 106 the request generated by the controller 102. The response assembly 110 is used by the patient 106 to generate the response and communicates the response to the controller 102. Example of response assemblies particularly useful herein are hand grip assemblies as described in detail in commonly assigned patent application Ser. No. 10/674,160 entitled Response Testing for Conscious Sedation Involving Hand Grip Dynamics filed on Sep. 29, 2003. The response assembly includes a handpiece which senses a dynamic variable of a hand grip response made by the patient to the request and communicates the dynamic variable to the controller which analyzes at least the dynamic variable to determine a level of sedation of the patient.

One method of integrating DC with the ARM and a Supervisory Shell is to limit maintenance rate increases based on the patient's responsiveness. For example, if the patient is unresponsive to ARM, the system will not allow the user to increase the MR, but if the patient is responsive there would be no ARM linked limits on increasing the MR. Alternatively, maintenance rate increase limits can be based on the patient's level of responsiveness. For example, if the patient responds to the stimuli within 5 seconds, the MR might be increased by 30 µg/kg/min in the case of propofol, if the response occurs between 5 and 10 seconds the MR can be increased by 20 µg/kg/min, and if the response occurs in greater than 10 seconds the MR can only be increased by a limited amount such as 10 µg/kg/min. This control function is illustrated in the flow chart provided as FIG. 21 where control steps 290, 292 and 294 correspond respectively to MR increases triggered by ARM response times of less than 5, 5 to 10 and 10 or more seconds.

Furthermore, the patient's response to ARM, or more specifically, loss of ARM response may be used as a Supervisory Shell feature in monitoring and adjusting the maintenance rate especially for long procedures. According to PK principals, over time even with a constant infusion rate, the concentration of a drug in the body will gradually increase. This can lead to unexpected over-dosage, and accompanying adverse events. Propofol labeling calls for a reduction in infusion rate 15-20 minutes after initiating a Maintenance Rate infusion. A Supervisory Shell, integrated into the DC can automatically perform this suggested reduction effectively maintaining a safe level of sedation. In one embodiment, as long as the patient is responsive to ARM, the integrated system will not perform an automatic reduction. However, after 15 minutes of continuous non-responsiveness, the system can reduce the maintenance bate by a fixed amount (5% for example). This is repeated every 15 minutes, as long as the patient remains non-responsive to ARM. As soon as the patient regains responsiveness the reductions are stopped. Should the patient lose responsiveness again, for 15 continuous minutes the reductions will start again. By using DC of this invention, these MR reductions will rapidly and effectively reduce the patient's level of sedation. Although 15 minutes was used in the above discussion, the amount of time before triggering a reduction in infusion can vary, and should be selected based on the pharmacokinetics of the drug being delivered.

The above discussion centers on DC and the delivery of propofol. However, the concept of DC can be applied to any intravenous drug. The equations will have to be adjusted to account for different pharmacokinetics (loading dose/maintenance rate relationships) and a different measure of "effect" will be required for non-sedatives.

G. Integration of DC and ARM with Patient Tuned Sedation

A further embodiment incorporates a patient-tuned sedation feature with DC. Since differences in effective analgesia or anesthesia dosages can be dramatic even among physically similar patients who are subjected to very similar pain-producing circumstances, it could be desirable to develop a system that incorporates patient input in the delivery of the drugs. The concept is to include the benefits of patient controlled sedation with the benefits of DC.

With regard to the level of analgesia or anesthesia that is needed by a particular patient at a particular time, it often has been suggested that the "best" pain expert for a particular patient is the patient himself or herself—as opposed to the patient's physician. While physicians may have the knowledge and experience that is needed to determine a suitable dosage range to meet the needs of a particular patient, it tends to be the patient, not the physician, who is the best judge of the dosage within the physician-set range that best serves the needs of the patient at a particular time and under the circumstances of the moment. The effectiveness of the administration of analgesia or anesthesia often can be enhanced when the dosing of the drug is being controlled by the patient—with safety considerations being kept in mind to prevent overdose. Accordingly, it is desired to provide a system which combines the benefits of DC with the benefits of patient controlled sedation.

The system in this embodiment may also incorporate the advantages of DC and ARM with advantages of patient controlled sedation to form another embodiment of the present invention—Patient Tuned System (PTS). In patient tuned sedation, the patient, with an ARM-like device, is acting as the depth of sedation sensor, essentially, closing the loop on sedation. The system would include all of the patient monitors currently in the sedation delivery system such as ECG, capnometry, pulse oximetry, and NIBP.

In one embodiment, the level of sedation that is desired for the Anesthetic Delivery System is the transition between moderate and deep sedation. This transition point is well defined by the patient's loss of responsiveness to ARM. The patient's loss of responsiveness to ARM corresponds with the point where a patient can no longer dose himself with a patient tuned sedation system. Essentially, the patient's responsiveness to ARM acts as a dose limiter so that when the patient loses responsiveness, the patient can't send any response to deliver more drug. Furthermore, there is a lock-out period that follows a patient's response, such as pressing a button to deliver additional drugs, to prevent the patient from overdosing himself.

In an embodiment of the invention, the Patient Tuned Sedation starts by having the clinician enter a "ballpark" maintenance rate along with the patient's weight. The system would begin by delivering an initiation loading dose calculated from DC in accordance with the invention. After a specified time period, typically 90 seconds, the ARM-like device sends a request for a patient's response. The request may be, for example, an audible signal such as "Squeeze your hand if you are feeling discomfort." The message may be repeated every 60 seconds.

If the patient responds quickly, for example within 3 seconds of the message, to the request by squeezing his hand, the PTS will increase the maintenance rate by 10 µg/kg/min, utilizing DC to rapidly achieve the new sedation level. At this point, the PTS will be locked out from increasing the maintenance rate for 60 seconds regardless of how many times the patient squeezes his hand. This acts as a safety precaution to prevent the patient from over-sedation. If the patient responds, less quickly, for example, between 3 and 10 seconds, the PTS would increase the maintenance rate by 5 µg/kg/min. If it took the patient a greater time to respond, for example more than 10 seconds, the PTS would not increase the maintenance rate, but would rather deliver a small bolus (~0.025 mg/kg).

In another embodiment, the maintenance rate increase could be larger, say 25 µg/kg/min for a response within 3 seconds, 12 µg/kg/min for responses between 3 and 10 seconds and a 0.1 mg/kg bolus for longer responses, but the lock-out period would be longer, on the order of 3 to 5 minutes.

If the patient does not respond within an allotted time (15 seconds), the PTS would not deliver any additional drug. Further, if the patient does not respond during 3 consecutive queries, the PTS would begin a slow decrease in the maintenance rate, for example, 5% every 15 minutes. This is intended to keep the non-responsive or deeply sedated patient from entering a state of general anesthesia.

Accordingly, by using a patient tuned sedation system, the patient acts as the depth of sedation monitor, essentially closing the loop on sedation.

Having described the invention in detail and by reference to specific embodiments thereof, it will be apparent that modifications and variations are possible without departing from the spirit and scope of the invention as defined by the following claims. The various embodiments described herein may be performed separately or together in any combination.

What is claimed:

1. A drug delivery system that delivers a loading dose and a maintenance rate of a drug to a patient, the system including an infusion pump and a controller, the controller being programmed such that the system performs the steps of:
    (a) calculating a loading dose based on the maintenance rate or a maintenance rate based on the loading dose;
    (b) administering the loading dose to the patient to achieve a desired level of effect;
    (c) administering the drug at a first maintenance rate to maintain the level of sedation; and
    (d) sensing the physiology of the patient wherein the controller is programmed to discontinue the step of administering the drug if adverse physiology or an adverse trend in physiology is detected.

2. The drug delivery system of claim 1 wherein the step of calculating a loading dose based on the maintenance rate or a maintenance rate based on the loading dose is based on a formula that correlates the maintenance rate and the loading dose recommended by the drug supplier.

3. The drug delivery system of claim 2 wherein the formula is based upon a linear interpolation of the maximum recommended loading dose and the maximum recommended maintenance rate.

4. The drug delivery system of claim 3 wherein the controller is programmed to calculate the loading dose based on the formula:

$$LD = 0.5 * W * (MR/75)$$

where, LD=Loading Dose (mg), MR=Maintenance Rate (µg/kg/min), W=Weight (kg) of the patient.

5. The drug delivery system of claim 3 wherein the controller is programmed to calculate the incremental loading dose based on the formula:

$$\text{Incremental } LD = 0.5 * W * (MR\_\text{new}/75) - LD\_\text{cum}.$$

6. The drug delivery system of claim 1 wherein the controller includes a setting to administer the loading dose by operating the infusion pump at an infusion rate approximately equal to the maximum infusion rate of the pump.

7. The drug delivery system of claim 1 wherein the controller includes a setting to administer the loading dose by administering the loading dose over a predetermined period.

8. The drug delivery system of claim 1 wherein the drug delivery system tracks the cumulative loading dose administered to the patient, wherein the cumulative loading dose is calculated based on the formula:

$$LD\_\text{cum}_x = LD\_\text{cum}_{x-1} + \text{amount of } LD \text{ currently delivered in sample } x.$$

9. The drug delivery system of claim 1 wherein the controller is programmed with a second maintenance rate whereupon the system:
    (a) calculates an incremental loading dose for the drug based on the second maintenance rate
    (b) administers the incremental loading dose to the patient to rapidly achieve the new desired level of effect; and
    (c) administers the drug at the second maintenance rate to maintain the new level of effect.

10. The drug delivery system of claim 9 wherein the controller is programmed to administer the incremental loading dose over a predetermined period.

11. The drug delivery system of claim 1 where the infusion pump delivers the drug at an infusion rate that can be set to zero for a period of time.

12. The drug delivery system of claim 11 wherein the controller is programmed to calculate the zero period of time based on the incremental loading dose.

13. The drug delivery system of claim 12 wherein the zero time period is calculated using the formula:

$$\text{Zero\_time} = 60 * 1000 * LD/(MR*W)$$

14. The drug delivery system of claim 1 wherein the controller includes a setting to deliver a transient bolus of the drug to temporarily increase in the patient's level of effect.

15. The drug delivery system of claim 1 wherein the controller is programmed to calculate a maintenance rate reduction by calculating the apparent maintenance rate at the time the adverse physiology or trend has cleared (physiology returns to normal), based on the formula:

$$MR\_apparent = 75 * LD\_cum/(0.5*W)$$

16. The drug delivery system of claim 1 wherein the system further includes an automated response monitoring system (ARM).

17. The drug delivery system of claim 16 wherein the system further includes a patient response input.

* * * * *